United States Patent
McKenzie, Jr.

(10) Patent No.: US 12,274,848 B1
(45) Date of Patent: *Apr. 15, 2025

(54) DELIVERY SYSTEM DEVICE AND METHOD FOR PHARMACEUTICAL IMPLANTATION FOR TIMED RELEASE

(71) Applicant: CEMStar, LLC, Tarpon Springs, FL (US)

(72) Inventor: Robert G. McKenzie, Jr., Tarpon Springs, FL (US)

(73) Assignee: CEMStar, LLC, Tarpon Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,457

(22) Filed: Sep. 20, 2023

Related U.S. Application Data

(60) Provisional application No. 63/409,012, filed on Sep. 22, 2022.

(51) Int. Cl.
*A61M 37/00* (2006.01)

(52) U.S. Cl.
CPC . *A61M 37/0069* (2013.01); *A61M 2202/0007* (2013.01); *A61M 2205/02* (2013.01)

(58) Field of Classification Search
CPC .............. A61K 9/0056; A61K 31/456; A61M 37/0069; A61M 2202/0007; A61M 2205/02
See application file for complete search history.

(56) References Cited

PUBLICATIONS

Li et al, The Control of Bead Diameter of Bead-on-String Electrospun Nanofibers and the Corresponding Release Behaviors of Embedded Drugs, Materials Science and Engineering C 74 ( 471-477 (Year: 2017).*
Srinivasarao K et al, International Journal of Research in Pharmacy and Chemistry, vol. 7, No. 2, pp. 141-147 (downloaded Nov. 9, 2024 at https://ijrpc.com/files/12-04-17/02.pdf).
Testopel (testosterone pellets) CIII Implantation techniques for Testopel, Brochure TP-05098/Dec. 2018 Endo Pharmaceuticals, Inc., Malvern, PA 19355 downloaded as www.testopel.com/_assets/pdfs/ImplantationGuide_digital.pdf on Nov. 8, 2024.
Testopel (testosterone pellets) CIII Package insert Endo USA, Malvern, PA 19355 Revised Mar. 2024 downloaded as https://d1skd172ik98el.cloudfront.net/48a33315-f594-4269-8043-8853d10fb7bf/567f802a-4a33-4fa0-b81c-936bef097178/567f802a-4a33-4fa0-b81c-936bef097178_source_v.pdf.

* cited by examiner

*Primary Examiner* — Carlos A Azpuru
(74) *Attorney, Agent, or Firm* — Brooke Schumm PA; Brooke Schumm, III

(57) ABSTRACT

The invention is a delivery system device and method for implantation of pharmaceuticals, such as hormones, including testosterone for military forces to increase stamina and aid in wound recovery, for timed release into a patient to be determined by a medical professional. This timed-release device will consist of an axially containing and longitudinally flexible elongated member having an axial wall of varying material, that wall consisting of a polymer dissolving according to a pre-determined schedule regulated by the dissolution rate of the polymer or polymer blend. The delivery system and method further prevents the extrusion or migration of the pellets from the site of implantation and allows for easier removal after the time of implant.

30 Claims, No Drawings

DELIVERY SYSTEM DEVICE AND METHOD FOR PHARMACEUTICAL IMPLANTATION FOR TIMED RELEASE

CROSS-REFERENCE TO RELATED APPLICATIONS

This application claims benefit of U.S. Provisional Application 63/409,012 filed on Sep. 22, 2022 and priority to that date.

BACKGROUND OF THE INVENTION

Field of Invention

The present invention relates to systems and methods for delivering pharmaceutical ingredients to treat animals and humans in a timed released manner and to prevent the migration of the pharmaceutical from the treatment site.

Background

In hormonal therapy, one method for treating low testosterone is to make a series of implants made from testosterone in one of its many salts, i.e. Testosterone, including testosterone cypionate, compressed into a pellet with a binding agent that releases over time, such as stearic acid. These pellets typically dissolve over the course of about 3 months making the active ingredient, Testosterone, available to the body and thereby increasing Testosterone levels in the patient. These loose pellets are dependent on the tissue in the body to hold the implant in place. These pellets can be purchased from several sources and/or compounded. Patient complaints are common because of the pellets being extruded from the injection site or the pellets migrating to other areas of the body.

The limitation in the current art of the pellet implantation device and method is that the device and method are dependent on the compression forces to make the pellet and the binding agent such as stearic acid break down over time in the body to release the active pharmaceutical ingredient, such as testosterone or one of its salt forms. This typically is about 3 months thereby requiring the patient to return for additional implantation. It is relatively impractical if not impossible to have a longer horizon than three months for a single pellet with a consistent pattern of release by that pellet under current technology. Even though a local anesthetic is used for example, for quarterly implantation, there is trauma at the injection site from the pellet implant and the area is sore which is uncomfortable for the patient leading to non-compliance for return visits over time.

No prior art proposes to use a trocar to insert one or more bioabsorbable sleeves calibrated to enable a pharmaceutical to be absorbed over a particular time containing one or more pellets to be absorbed upon the sleeve degradation.

SUMMARY OF THE INVENTION

The invention is a delivery system device and method for implantation of pharmaceuticals, such as hormones, including testosterone for military forces to increase stamina and aid in wound recovery, for timed release into a patient to be determined by a medical professional. This timed-release device will consist of an axially containing and longitudinally flexible elongated member having an axial wall of varying material, said wall consisting of a polymer dissolving according to a pre-determined schedule regulated by the dissolution rate of the polymer or polymer blend. The delivery system and method further prevents the extrusion or migration of the pellets from the site of implantation and allows for easier removal after the time of implant.

Objectives of the Invention

Currently Military forces have used implanted hormones in pellets to boost the testosterone levels in its forces for stamina, aggression, and help with wound recovery. The current length of time these pellet implants are active is short: up to 3 months. This invention which contemplates a combination to achieve a longer acting horizon for administration of a pharmaceutical product would allow the use of implantation for longer field deployments preferably on an annual basis.

The invention proposes to have manufactured a sleeve in the nature of a sausage casing or a woven suture-like material, including one available from River Point Medical, Portland, Oregon, made of a bioabsorbable material, and proposes to put in that material pellets with pharmaceutical products and carriers so that the combination will prevent the migration of these pellets and hold them in place either one pellet next to each other or spaced apart from each other with polymer spacers in a manner that enables the pharmaceutical product to be absorbed inside tissues of the body over predictable and pre-determined periods of time. The sleeve or strand can be heat-shrunk to better contain the pellets.

By extending the time from a pellet implant every three months to administration of strands by one or more trocars once a year a patient would be more compliant yielding the desired benefits of stamina, aggression, and help with wound recovery for a longer period of time and allowing a health care provider to treat more patients.

By using a polymer sleeve or suture like material for a sleeve, the "strand" can accurately be placed in the body prevent expulsion or migration of loose pellets.

It is further desired that an elongated member with pellets be ridged axially to allow the expulsion of the member while maintaining distance from each pellet with a bioabsorbable spacer maintaining distance between pellets for better dissolution.

This elongated member with pellets being ridged axially would also allow for easy retraction of the pellets to adjust the treatment to reach the desired therapeutic blood levels or terminate treatment by removing the strand of implants.

The spacer material used with the pharmaceutical pellets could be echogenic allowing for visualization of the stand using ultrasound.

The spacer material used with the pharmaceutical pellets could be made with a contrast agent allowing for visualization of the strand using CT or MRI scanning techniques.

A further object of the present invention is to provide a delivery system pharmaceutical therapy that faster and easier than the present system.

Another objective of the present invention is to cause a minimum of trauma to the tissue.

Yet another objective of the delivery system is to allow a controlled release of the active pharmaceutical ingredient into tissue allowing for accurate placement of the implant.

In another aspect the selected bio-compatible material is selected by polymer blend to accurately breach over time allowing the pharmaceutical pellets to begin to slowing release over time.

In another aspect the selected bio-compatible material is selected and layered or increased wall thickness to accurately breach over time.

A further embodiment is active pharmaceutical ingredient embedded in bio-absorbable polymer.

The polymer "Sleeve" or "strand" can be perforated to allow for controlled release of the pharmaceutical pellets.

The polymer "sleeve" or "strand" containing the pharmaceutical can be sterilized prior to implantation.

DETAILED DESCRIPTION OF THE INVENTION

In accordance with one embodiment of the invention, it is proposed that four strands be implanted as follows. The active pharmaceutical ingredients can be as previously referenced, but the preferred embodiment contains testosterone or a salt Aa 1. Strand #1 contains PGA 100% perforated with holes that allow enzymes to break down the steric acid/testosterone pellet 0-3 month delivery.
2. Strand #2 contains PGA 80% and PLA 20% this dissolves in 3 months at which time the steric acid/testosterone pellets will dissolve over 3 months giving you 3-6 months of delivery.
3. Strand #3 contains PGA 50% and PLA 50% this dissolves in 6 months at which time the steric acid pellets will dissolve over 3 months giving you 6-9 month of delivery.
4. Strand #4 contains PGA 10% and PLA 90% (or 100% Polydioxanone (PDO) that dissolves in 9 months then steric acid pellets will dissolve for the last 3 months giving you 9-12 months of delivery.

A variation of this alternative is to lengthen one end of Strand #2 and perforate it. Any strand could be potentially perforated to alter bioabsorption to a more rapid pace.

In another embodiment, a longitudinally flexible elongated member with at least partial ridges arranged substantially axially made of material which is bio-absorbable in living tissue is provided for insertion into the body, for example muscle tissue, for sustained release of pharmaceutical ingredients. Pharmaceutical products means pharmaceutical ingredients which terms mean and include FDA approved drugs, drugs compounded by a pharmacist, and API's (Active Pharmaceutical Ingredients) or other pharmacy related items. A plurality of pharmaceutical ingredients in the form of pellets can be encapsulated and positioned in a predetermined array in the member in the desired spaced relationship.

Those Active Pharmaceutical Ingredients can include any pharmaceutical agent, including diet supplements with mammalian effect, including LDN (low dose naltrexone), disulfram and others such as pain medications optimized for timed release.

The substantially axially, semi-ridged elongated member may be made of any natural and/or synthetic bio-compatible and bio-absorbable materials. Natural and synthetic polymers and copolymers can be used. Examples of synthetic bio-absorbable polymer materials are polyglycolide and polylactide, polydioxanone and polymeric materials and their equivalents. Such polymeric materials and their equivalents are more fully described in U.S. Pat. Nos. 3,565,869, 3,636,956, 4,052,988 and European Patent application 30822. The materials in this paragraph are referenced generally as "bioabsorbable polymeric materials."

When the term stearic acid is used, its meaning is intended to cover all pharmaceutical carriers known in the art that are formulated with a particular pharmaceutical to both have the pharmaceutical carrier dissolve at a pre-determined rate and the pharmaceutical be absorbed at a pre-determined rate. The strand will have the purpose of keeping the pellets in one location in the body so that the pellets do not migrate pending dissolution and absorption of the pharmaceutical in the pellet.

The hormone testosterone or one of its salts can be pressed into a pellet with stearic acid or other binding material to give a pellet that is consistently released over 3 months. A sleeve would be closed off at one end, preferably with a heat source, and the pellets loaded into the sleeve by themselves or with polymer spacers in between them, then sealed at the other end, preferably with a heat source. The heat source can be an iron, or soldering iron or heat sealer. Other sealing methods such as glue can be used but must be body soluble and non-toxic. The sleeves could be made of the following materials to give the desired dissolution times post sterilization. The materials in this invention are available from, among other sources, Corbion Biotech, Inc. in Lenexa, Kansas and Sigma-Aldrich of St. Louis, Missouri.

TABLE 1

| Material | Release Time | Testosterone Release |
|---|---|---|
| 100% Glycolide Perforated | No delay in the breakdown of the pellet | 0-3 months |
| 80% Polyglycolic Acid (PGA) & 20% Polylactide Acid (PLA) | 3 month until the strand is breached | 3-6 months |
| 100% Polydioxanone (PDO) | 6 months until the strand is breached | 6-9 months |
| 90% Lactide & 10% Glycolide | 9 months until the strand is breached | 9-12 months |

This is an example of the materials and not all inclusive of materials the invention can utilize.

Another way to vary the above times is to vary the thickness of the polymer wall composing the strand. In general a thickness of 0.05 mm 0 is contemplated but it could be 0.02 mm. The key is that the inside diameter of the strand must be larger than the outside diameter of the pellet. A typical outside diameter of the pellets is 3.0 mm, 3.2 mm, 4.3 mm, 4.5 mm and 5.62 mm in diameter. For women, the smaller sizes of 3.0-3.2 mm would be typical and for men, the larger sizes would be typical. The length of the pellets within the strand would be typically 9 mm and would be cylindrical. The typical strand would have 10-12 pellets and the preferable implant of the strands would be four strands with the varying release referenced in Table 1. The strand can be shrink-wrapped over the pellet. Normally one size of pellet would be used. For variations in body weight, more or less pellets would be loaded in the strand. Other ways to vary the dissolution rates, in addition to varying wall thickness, would be to vary the polymer ratio, encase one strand within another with the inside strand having an inside diameter larger than the outer diameter of the pellet, and varying the texture of the strand as woven versus smooth.

A manufacturer of strands suitable for the contemplated invention are available from Theragenics Corporation of Buford, Georgia.

In between the encapsulated pellets, there can be placed a bioabsorbable spacer made with air bubbles or contrast materials commonly used in the body to allow for visualization via ultrasound, CT or MRI scans. This can show placement of the stranded material in the body and dissolution of the strand over time. The spacer can cooperate with the strand and the pellets in the time release of pharmaceutical material.

A pre-sterilized kit containing sterile strands with pharmaceutical pellets and a sterile trocar will save the health care provider time. The trocar is used to insert the strand and then retracted leaving the strand in its desired location within the body. The technology for such insertion, leaving and retraction is standard in brachytherapy used for implantation of radioactive seeds. The strands can be sterilized with gamma sterilization or e-beam sterilization or other known methods.

The small diameter of the strands and reduction to one application per year will reduce the trauma to patient and encourage compliance with the therapy.

The timed released of the pharmaceutical pellets can also be achieved as follows.

The first polymer sleeve (also called a "strand") will have perforations allowing the enzymes in the tissue to enter and dissolve the pellets pressed with stearic acid over a period of 3 months. The second strand will have a polymer ratio of Polylactide Acid (PLA) to Polyglycolic Acid (PGA) so that that second portion of the strand will dissolve over 3 months during the period of three months to six months after the initial implantation of the strand in a patient during which period the pharmaceutical pellets will be absorbed resulting in an additional 3 months of release to reach 6 total months of therapy. The third strand will have a polymer of Polydioxanone in the sleeve so that the strand will dissolve over 3 months during the period of six months to nine months after the initial implantation of the strand in a patient during which period the pharmaceutical pellets will be absorbed resulting in an additional 3 months of release to reach 9 total months of therapy. The fourth strand will have a polymer ratio of Polylactide Acid (PLA) to Polyglycolic Acid (PGA) so that that fourth strand will dissolve over 3 months during the period of nine months to twelve months after the initial implantation of the strand in a patient during which period the pharmaceutical pellets will be absorbed resulting in an additional 3 months of release to reach 12 total months of therapy. In sum, with additional implantation under this enablement, the device will achieve a total of 12 months of active pharmaceutical ingredient release by the combination of the selection of sleeve material and time-release pellet containing at least one pharmaceutical. As stated, one contemplated enablement is the release of testosterone hormone over the course of one year. As a practical matter, multiple strands are easier to work with, but in theory there could be one long strand of one or more polymers. As an alternative to the above use of various polymers one could use a single polymer and adjust the thickness of the strand to affect the dissolution rate. For example using a Polyglycolic Acid (PGA) strand with a wall thickness of 0.002 inches (0.051 mm) perforated for the release of the compressed testosterone pellet in steric acid to give a 3 months dissolution rate, a 0.002 inch (0.051 mm) non-perforated strand for the release of the compress testosterone pellets for 6 months dissolution rate, a 0.004 inch (0.01 mm) non perforated strand for 9 months dissolution rate and a 0.006 inch (0.015 mm) non perforated strand for 12 month dissolution rate. By keeping the polymer material the same you reduce the expense of manufacturing.

Other Modes of the Invention

Besides Polylactic Acid (PLA) or Polyglycolic Acid (PGA), co-polymer or self-reinforcing composites can be used. By using one or more combinations an absorption time can be extended past 5 years.

TABLE 2

| Polymer | Melting Point (° C.) | Glass-Transition Temp. (° C.) | Modulus (Gpa) (gigapascals) | Degradation Time (months) |
|---|---|---|---|---|
| PGA | 225-230 | 35-40 | 7.0 | 6-12 |
| L-PLA | 173-178 | 60-65 | 2.7 | >24 |
| DL-PLA | Amorphous | 55-60 | 1.9 | 12 to 16 |
| PCL | 58-63 | (−65)-(−60) | .4 | >24 |
| PDO | 110 | (−10)-0 | 1.5 | 6-12 |

TABLE 3

Biodegradable polymers, properties and degradation time

| Polymer combination | Ratio of $1^{st}$ polymer to $2^{nd}$ polymer in copolymer | Degradation Time (months) |
|---|---|---|
| 1) PGA | PGA to | 6-12 |
| 2) TMC | TMC ratio | |
| TMC = trimethenecarbonate | 85:15 | |
| DLPLG = Poly(D,L-lactide-co-glycolide) | Lactide to glycolide | 4-5 |
| DLPLG 75/25 | ratio 75:25 | |
| DLPLG 65/35 | Lactide to glycolide ratio 65:35 | 3-4 |
| DLPLG 50/50 | Lactide to glycolide ratio 50:50 | 1-2 |

Other alternatives that can be used are referenced in U.S. Pat. No. 7,942,803 issued May 17, 2011.

TABLE 4

| Polymer | Absorption Time |
|---|---|
| *SR PLLA | >5-6 years |
| **PLLA | >5 years |
| ***P(D/L) LA 70/30 | 2-3 years |
| PLA/PGA (PLGA) 80/20 | 1-2 years |
| *P(D/L) LA 96/4 | 2 years |
| *SR PGA | 0.5-1 years |
| PDS (polydioxanone) | 2 months |
| PGA | 1-2 months |
| Perforated PGA | Time Zero-3 months |

*SR is Structure Reinforced
**PLLA is the L-Isomer of PLA
***(D/L) is the D and L isomer A variation to the system to obtain the same results is changing the ratios of the polymer blend to layer the same or another polymer blend in the axial sleeve wall to slow the access of body fluids to the pellets by delaying dissolution of the wall and accordingly absorption or the pharmaceutical material in the pellet. Alternatively, one can increase the axial wall thickness to achieve the desired delayed release of the pharmaceutical pellets. Alternatively, the pharmaceutical pellets themselves can be designed to be bioabsorbed at different times as the wall is bioabsorbed.

In implementing the invention, one end of the sleeve is heat sealed. The pellets are placed into the sleeve with or without spacers and the other end of the sleeve is sealed. The strand is heated, preferably baked in an oven to shrink the strand over the pellets making the strand that in total has a substantially axial wall, with a semi-ridged and longitudinally flexible elongated member. At this point the strand can be inserted into another sleeve and the process repeated to give a double wall strand, thereby halving and therefore slowing the dissolution rate. This can also be achieved during the extrusion process of the strand material to double the wall thickness.

Different wall thicknesses of different materials with varying dissolutions rates can be combined so that more nuanced release can be achieved.

Thereafter, the sleeve is inserted in a trocar that encompasses the sleeve for insertion into a patient. Trocar applicators will need to be sized to the strands so that the trocar will have the proper interior diameter and length for application.

An alternative to the sleeve is to embed the pharmaceutical pellets into the polymer, co-polymer or structure reinforcement.

The delivery system and method further prevents the extrusion or migration of the pellets from the site of implantation and allows for easier removal after the time of implant.

The embodiments represented herein are only a few of the many embodiments and modifications that a practitioner reasonably skilled in the art could make or use. The invention is not limited to these embodiments. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention as claimed.

The invention claimed is:

1. A device for extended release of pharmaceutical products comprising:
    an implantable bioabsorbable elongated member appearing as a strand having at least one sleeve slideable into a trocar for implantation;
    said bioabsorbable elongated member being enabled to contain time-release pellets containing at least one pharmaceutical material;
    said elongated member containing time-release pellets having a pre-determined pharmaceutical schedule for time release of said at least one pharmaceutical material from said elongated member containing time-release pellets;
    said bioabsorbable elongated member being bioabsorbable;
    said bioabsorbable elongated member having multiple varied polymeric strands having at least one layer of polymeric material, each said strand containing said time-release pellets, each said strand being formulated from a varying combination of bioabsorbable polymeric materials set to dissolve at varying times so that by the cooperation of the rate of dissolution of each said polymeric strand and the rate of time release of the time-release pellets contained within each said polymeric strand result in the time release of said at least one pharmaceutical material in each said strand corresponding to said pre-determined pharmaceutical schedule.

2. The device for extended release of pharmaceutical products set forth in claim 1 wherein said bioabsorbable elongated member is axially rigid and radially flexible.

3. The device for extended release of pharmaceutical products set forth in claim 1 wherein said bioabsorbable elongated member has sufficient radial flexibility to maintain locational accuracy.

4. The device for extended release of pharmaceutical products set forth in claim 1 wherein said bioabsorbable elongated member is longitudinally flexible.

5. The device for extended release of pharmaceutical products set forth in claim 1 wherein said bioabsorbable elongated member is laterally flexible.

6. The device for extended release of pharmaceutical products set forth in claim 1 wherein said bioabsorbable elongated member contains pellets positioned at various intervals, said pellets containing any one of testosterone or a salt of testosterone.

7. The device for extended release of pharmaceutical products set forth in claim 1 wherein said bioabsorbable elongated member contains pellets positioned at various intervals.

8. The device for extended release of pharmaceutical products set forth in claim 1 wherein said bioabsorbable elongated member having at least one sleeve is perforated to allow instant access to the pharmaceutical pellets by enzymes and phagocytes in the absorption process in living tissue.

9. The device for extended release of pharmaceutical products set forth in claim 1 wherein the bioabsorbable elongated member having at least one sleeve is absorbed in living tissue from a range of initial placement to over 60 months.

10. The device for extended release of pharmaceutical products set forth in claim 1 wherein the bioabsorbable elongated member having at least one sleeve is absorbed in living tissue from a range of initial placement to one month, to two months, to three months or any number of months up to sixty months.

11. The device for extended release of pharmaceutical products set forth in claim 1 wherein the bioabsorbable elongated member having at least one sleeve is absorbed in living tissue beginning at a set point after initial placement over a range of a set period of up to 5 years.

12. The device for extended release of pharmaceutical products set forth in claim 1 wherein the bioabsorbable elongated member having at least one sleeve is sealed on both ends preventing products of bodily fluids and cells from dissolving the time-release pellets prematurely.

13. The device for extended release of pharmaceutical products set forth in claim 1 wherein the one or more materials constituting the bioabsorbable elongated member having at least one sleeve is selected from the group of synthetic bioabsorbable polymer materials.

14. The device for extended release of pharmaceutical products set forth in claim 1 wherein the one or more materials constituting the bioabsorbable elongated member having at least one sleeve is selected from the group of polylactic acid (PLA), polyglycolic acid (PGA), SR PLLA, PLLA, P(D/L) LA 70/30, PLA/PGA (PLGA) 80/20, P(D/L) LA 96/4, SR PGA, PDS (polydioxanone), PGA, perforated PGA, or composites or co-polymers of materials in this group.

15. The device set forth in claim 1 wherein the polymeric material is selected in varying amounts and ratios from the group of glycolide, lactide, and polydioxanone.

16. The device for extended release of pharmaceutical products set forth in claim 1 wherein the one or more materials constituting the bioabsorbable elongated member having at least one sleeve is selected from polydioxanone.

17. The device for extended release of pharmaceutical products set forth in claim 1 wherein the one or more materials constituting the bioabsorbable elongated member having at least one sleeve is selected from structural reinforcement materials.

18. The device for extended release of pharmaceutical products set forth in claim 1 wherein the one or more materials constituting the bioabsorbable elongated member having at least one sleeve contains pharmaceutical pellets.

19. The device for extended release of pharmaceutical products set forth in claim 1 wherein the one or more materials constituting the bioabsorbable elongated member having at least one sleeve contains pharmaceutical pellets containing stearic acid or other binding chemicals.

20. The device for extended release of pharmaceutical products set forth in claim 1 wherein the one or more materials constituting the bioabsorbable elongated member having at least one sleeve is echogenic.

21. The device for extended release of pharmaceutical products set forth in claim 1 wherein the one or more materials constituting the bioabsorbable elongated member having at least one sleeve is visible with a CT scanner.

22. The device for extended release of pharmaceutical products set forth in claim 1 wherein the one or more materials constituting the bioabsorbable elongated member having at least one sleeve is visible with an MRI scanner.

23. The device for extended release of pharmaceutical products set forth in claim 1 wherein the one or more materials constituting the bioabsorbable elongated member having at least one sleeve can be gamma sterilized.

24. The device for extended release of pharmaceutical products set forth in claim 1 wherein the one or more materials constituting the bioabsorbable elongated member having at least one sleeve can be electron beam sterilized.

25. The device for extended release of pharmaceutical products set forth in claim 1 wherein the one or more materials constituting the bioabsorbable elongated member having at least one sleeve can be steam sterilized.

26. The device for extended release of pharmaceutical products set forth in claim 1 wherein the one or more materials constituting the bioabsorbable elongated member having at least one sleeve can be layered to increase absorption time.

27. The device for extended release of pharmaceutical products set forth in claim 1 wherein the one or more materials constituting the bioabsorbable elongated member having at least one sleeve can be extruded with an increased wall thickness to increase absorption time.

28. The device for extended release of pharmaceutical products set forth in claim 1 wherein said bioabsorbable elongated member having at least one sleeve containing pellets can be provided as a sterile kit containing a trocar for the implantation of the sleeve into the patient.

29. The device for extended release of pharmaceutical products set forth in claim 1 wherein said bioabsorbable elongated member having at least one sleeve containing pharmaceutical pellets can be used to size the internal diameter of the trocar to reduce trauma to the patient.

30. The device for extended release of pharmaceutical products set forth in claim 1 wherein said bioabsorbable elongated member having at least one sleeve containing pharmaceutical pellets has pellets of varying bioabsorbability within said elongated member.

* * * * *